United States Patent
Joyce et al.

(10) Patent No.: US 6,548,059 B1
(45) Date of Patent: Apr. 15, 2003

(54) PROMOTION OF PROLIFERATION OF ADULT CORNEAL ENDOTHELIAL CELLS

(75) Inventors: Nancy C. Joyce, Marlborough, MA (US); Ko-Hua Chen, Taipei (TW); Tadashi Senoo, Tochigi (JP)

(73) Assignee: The Schepens Eye Research Institute, Inc., Boston, MA (US)

( * ) Notice: Subject to any disclaimer, the term of this patent is extended or adjusted under 35 U.S.C. 154(b) by 0 days.

(21) Appl. No.: 10/030,580

(22) PCT Filed: Jul. 24, 2000

(86) PCT No.: PCT/US00/40471
§ 371 (c)(1),
(2), (4) Date: Jan. 9, 2002

(87) PCT Pub. No.: WO01/06843
PCT Pub. Date: Feb. 1, 2001

Related U.S. Application Data

(60) Provisional application No. 60/145,171, filed on Jul. 22, 1999.

(51) Int. Cl.$^7$ ................. A01N 63/00; A61K 39/00; C12N 5/08; C12N 5/00
(52) U.S. Cl. ................. 424/93.7; 424/198.1; 435/371; 435/384
(58) Field of Search ................. 424/93.7, 198.1, 424/371, 384

(56) References Cited

U.S. PATENT DOCUMENTS 5,104,787 A 4/1992 Lindstrom et al. ............. 435/1

OTHER PUBLICATIONS

Tadashi Senoo, "Stimulation of Corneal Endothelial Cell Proliferation by Interleukins and Complete Mitogens", Dokkyo Journal of Medical Sciences, vol. 22 pp. 159–170 (1995).*

Ko–Hua Chen et al., "TGF–β2 in Aqueous Humor Suppresses S–Phase Entry in Cultured Corneal Endothelial Cells", Investigative Ophthatlmology & Visual Science, vol. 40, No. 11, pp. 2513–2519 (1999).

Tadashi Senoo, "Stimulation of Corneal Endothelial Cell Proliferation By Interleukins and Complete Mitogens", Dokkyo Journal of Medical Sciences, vol. 22, pp. 159–170 (1995).

Nancy C. Joyce et al., "Mitotic Inhibition of Corneal Endothelium in Neonatal Rats", Investigative Ophthalmology & Visual Science, vol. 39, No. 13, pp. 2572–2583 (1998).

* cited by examiner

Primary Examiner—Christopher R. Tate
Assistant Examiner—Randall Winston
(74) Attorney, Agent, or Firm—Weingarten, Schurgin, Gagnebin & Lebovici LLP

(57) ABSTRACT

Disclosed is a method of stimulating adult corneal endothelial cell proliferation, which includes incubation of corneal endothelium to a mitogen-containing medium and then to an agent that interrupts cell-cell contacts in the adult corneal endothelial cells, and subsequently, as needed, further incubation in the mitogen-containing medium. The cell-cell contact-interrupting agent is preferably a calcium chelator.

12 Claims, 2 Drawing Sheets

FIG. 1A
FIG. 1B
FIG. 1C
FIG. 1D
FIG. 1E
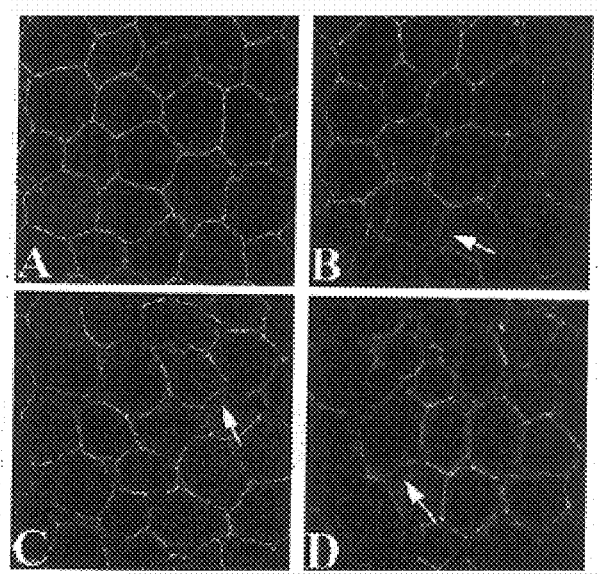
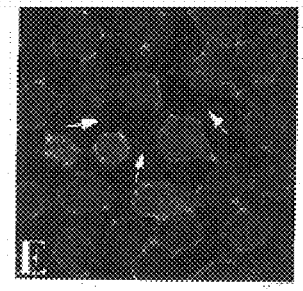
FIG. 2A
FIG. 2B
FIG. 2C
FIG. 2D
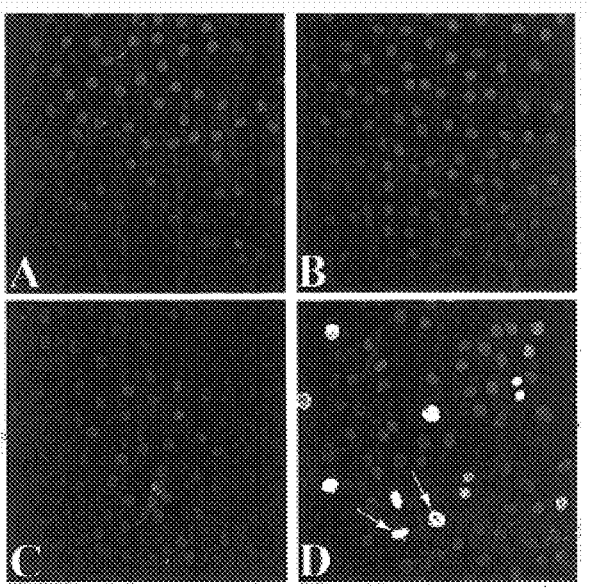

PROMOTION OF PROLIFERATION OF ADULT CORNEAL ENDOTHELIAL CELLS

CROSS REFERENCE TO RELATED APPLICATIONS

This application claims priority from U.S. Provisional Application No. 60/145,171, filed on Jul. 22, 1999, and International Application No. PCT/US00/03531, entitled GROWTH MEDIUM FOR HUMAN CORNEAL ENDOTHELIAL CELLS, filed on Feb. 11, 2000, which are fully incorporated herein by reference.

STATEMENT REGARDING FEDERALLY SPONSORED RESEARCH OR DEVELOPMENT

The work leading to the present invention was supported in part by federal funding under grant number NEI RO1 EY05767. Therefore, the U.S. government may have certain rights in this invention.

BACKGROUND OF THE INVENTION

Corneal endothelial cells are different from vascular and pulmonary "endothelial cells" as they have a different embryonic tissue origin. Human corneal endothelial cells do not normally proliferate in vivo to replace those lost due to cell injury or death. Growth of these cells in culture is also extremely limited. This can be a serious problem as age, diseases such as glaucoma and diabetes, and ocular surgical procedures, such as laser vision correction and cataract extraction and intraocular lens implantation, cause an accelerated loss of these precious cells. There are no medical treatments for corneal diseases resulting from endothelial cell loss. Currently, corneal transplantation is the only way to restore normal vision.

The relative ability of corneal endothelial cells to proliferate in vivo and in culture appears to be a function of age; i.e., embryonic corneal endothelial cells and cells from neonates will proliferate much more readily than cells from children and adults. In a few cases, researchers have been able to culture cells from older donors, but growth has been supported by seeding the cells onto an artificial matrix, such as chondroitin sulfate/laminin, or onto extracellular matrix secreted by corneal endothelial cells from cows, one of a number of species whose corneal endothelial cells do grow readily in culture. A reliable way of growing and/or supporting human corneal endothelial cells, whether in vitro or in vivo, would be highly desirable. In particular, there remains a need for stimulating proliferation of adult corneal endothelial cells.

SUMMARY OF THE INVENTION

The invention provides a new source of corneal endothelial cells for use in research and treatment of injured or diseased corneal endothelium. In particular, the invention enables the growth/proliferation of human corneal endothelial cells from adult humans, preferably those aged fifty or more years.

One aspect provides a simple, yet effective method of stimulating or promoting the proliferation of adult corneal endothelial cells, whether in vitro or in vivo. The invention encompasses exposing corneal endothelial cells to an agent that interrupts cell-to-cell contact, also called "cell-cell adhesion" or "cell-cell contact". Such cell-cell contact interruption step preferably is sandwiched between two incubation or exposure steps, in which adult-derived corneal endothelial cells are exposed to at least one growth factor, optionally in a growth medium. "Growth factor" refers to any factor that induces a corneal endothelial cell to enter the cell cycle and thus to proliferate. Exemplary growth factors include, but are not limited to, e.g., one or more mitogen(s) such as epidermal growth factor (EGF), fibroblast growth factor (FGF), and/or nerve growth factor (NGF). Other growth factors effective for corneal endothelial proliferation are known in the art and may be used in the invention.

The agent used to interrupt cell-cell contacts may be a calcium chelator such as ethylenediaminetetraacetic acid (EDTA), a known chelator of calcium and magnesium ions previously used in many laboratories to release cultured cells from contact inhibition. When added to a corneal culture medium, EDTA released cells from contact inhibition and promoted proliferation in corneal endothelium from older donors. Based on the observations reported here, it is expected that corneal endothelium from older individuals will divide in situ by exposing them to positive growth factors under conditions in which cells have been transiently released from contact inhibition. Human corneal endothelial cell density decreases with age (1,2), indicating that these cells do not replicate sufficiently to replace dead or injured cells. Transfection studies using viral oncoproteins have demonstrated that human corneal endothelium has an intrinsic high proliferative capacity (3,4). The fact that endothelial cells possess the capability to divide, but normally do not replicate in vivo, suggests that they are actively maintained in a non-replicative state. Cell cycle studies indicate that human corneal endothelial cells in vivo are arrested in the G1-phase of the cell cycle (5,6). Among the factors that may be responsible for maintaining these cells in G1-phase arrest, are a lack of available positive growth factors (7) and the presence in aqueous humor of transforming growth factor-$\beta$2 (TGF-$\beta$2), which has been found to suppress S-phase entry in cultured corneal endothelial cells (8,9). In addition, studies of the developing cornea in neonatal rats suggest that a contact inhibition-like mechanism may actively suppress replication in the mature endothelial monolayer (10). Other evidence for cell contact-mediated regulation of proliferation is that corneal endothelial cells will divide in response to wounding (11,12). In tissue culture and in organ cultured corneas, only endothelial cells adjacent to the wound edge or cells that have migrated into the wound bed will proliferate, demonstrating the importance of releasing cell-cell contacts in order to promote proliferation. Formation of cell-cell contacts or adhesions is mediated by a number of proteins that are associated with different types of junctional complexes, including cadherins (13) (adhering junctions), ZO-1 (14) (tight junctions), and connexin-43 (15) (gap junctions). These proteins all require calcium for maintenance of their adhesion function. In low-calcium environments, junctional complexes mediated by these proteins disassemble and cell-cell contact is broken. Exposure of the corneal endothelium to calcium-free medium causes disruption of apical junctional complexes, increased transendothelial perfusion, and corneal edema (16–18). These changes can be reversed by replacing calcium in the medium (17,18), or by exposing cells to ionophores that release intracellular calcium stores(18).

DESCRIPTION OF THE DRAWINGS

FIGS. 1A–E shows representative micrographs demonsatrating the dose- and time-dependent effect of a non-lethal amount of EDTA on cell-cell contacts in a corneal endothelium culture;

FIGS. 2A–D depict the Ki67-staining patterns of corneal endothelial cells in corneal pieces subjected to different treatment regimes and/or culture conditions.

DETAILED DESCRIPTION OF THE INVENTION

Figure 3A:
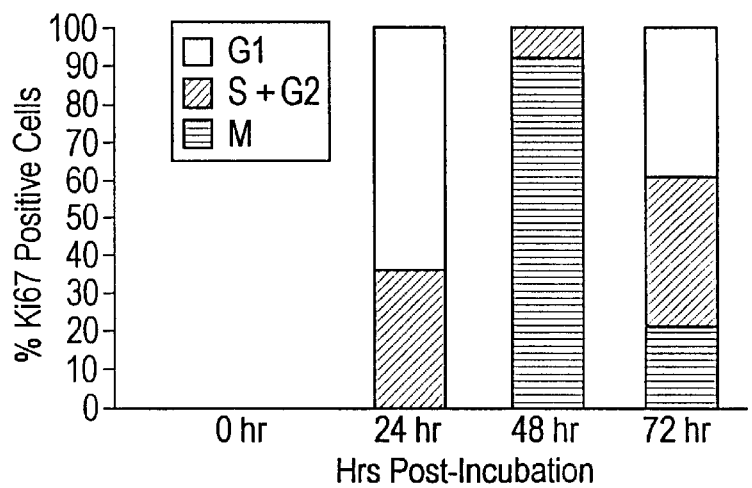
FIGS. 3A–C illustrate the effects of EDTA treatment on cell cycle kinetics (A), and a determination of the optimal pre-incubation time (B) and the optimal post-incubation time (C), by determining the percent (%) of Ki67-positive cells exhibiting staining patterns for G1 phase, S/G2 phase, or mitosis.

Previous studies from this laboratory (19) have demonstrated that corneal endothelium from older donors (>50 years old) is capable of proliferation in response to a mechanical wound. Cells from older donors responded in fewer numbers and entered the cell cycle more slowly than those from younger donors (approximately ≦30 years old), when corneas were cultured in medium containing 10% serum and 20 ng/ml fibroblast growth factor (FGF). Addition of approximately 10 ng/ml epidermal growth factor (EGF) to this medium induced significantly more older cells to proliferate and increased the rate of cell cycle entry. Nerve cell growth factor may also be added for better results. As in previous studies, only cells within the wound bed or at the wound edge proliferated. Together, these data suggest that endothelial cells from older donors can proliferate if cell-cell contacts are broken by wounding and if given sufficient mitogenic stimulation. The results reported herein definitively show, for the first time, that it is possible to induce proliferation in the endothelium without mechanical wounding of the monolayer. Preferably ethylenediamine tetraacetic acid (EDTA) or ethylene glycol-bis[βaminoethylether]-N,N,N',N'-tetraacetic acid (EGTA) can be used to release adult corneal endothelial cells from cell-cell contacts and to promote their proliferation in, e.g., an organ culture model.

It has now been observed that EDTA releases corneal endothelial cell-cell contacts in a dose- and time-dependent manner. At the doses and incubation times tested in the experiments described herein, EDTA did not induce significant cell death. Preincubation in culture medium alone (without EDTA), for about 6–24 hrs, preferably 12–24 hours, was needed for endothelial cells to efficiently initiate proliferation in response to subsequent EDTA treatment. The endothelium of corneas incubated in mitogen-containing medium for up to 108 hrs without EDTA treatment did not stain for Ki67. EDTA at 2.0 mg/ml for 60 minutes appeared optimal and stimulated 16–18% of the cells to proliferate. Ki67-positive mitotic figures were visible 48 hrs after exposure to EDTA. Formation of daughter cells was visible after double-staining for the Ki67 and ZO-1 markers.

Thus, the invention encompasses a method of stimulating proliferation of adult corneal endothelial cells, comprising exposing the corneal endothelial cells to an effective amount of at least one growth factor that promotes proliferation of corneal endothelial cells; and subsequently exposing the corneal endothelial cells to an effective amount of at least one agent that promotes interruption of cell-cell contacts between adjacent corneal endothelial cells. The method further comprises, as needed, and subsequent to the cell-cell contact interrupting step, exposing the corneal endothelial cells again to the at least one growth factor. In a preferred embodiment, the interruption step should result in cell-cell contact interruption in at least 15%, preferably at least 50%, most preferably at least 80%, of the corneal endothelial cells exposed to the interruption agent.

The invention also relates to a new formulation of culture medium which is being successfully used to stimulate the proliferation of adult (>50 years of age) donor human corneal endothelial cells in culture directly on tissue culture plastic. The new formulation includes: a serum-free cell culture medium comprising insulin, transferrin, and selenium; fibroblast growth factor (pituitary); epidermal growth factor; nerve growth factor; an antibiotic antimycotic solution; and a calcium chelator. Preferably the chelator is EDTA or EGTA, preferably in an amount of about 0.02–3.0 mg/ml, advantageously 0.2–2.0 mg/ml. Further details of the formulation, with respect to the non-chelator components, are described in International Application No. PCT/US00/03531, filed on Feb. 11, 2000, incorporated herein by reference.

Prior to the development of the present formulation, studies had been conducted to test the ability of adult corneal endothelial cells to grow on an artificial matrix (1% chondroitin sulfate/1% collagen) and on bovine or rabbit corneal endothelial cell matrix. Better growth was obtained on the artificial matrix, but cell shape frequently differed from normal. The new formulation of growth medium makes it possible to grow cells from adult donors directly on tissue culture plastic and retain normal polygonal shape, and to stimulate their proliferation.

The invention is further described with reference to the following, non-limiting example:

EXAMPLE I

Materials and Methods

Human Corneal Tissue

Donor human corneas were obtained from National Disease Research Interchange (Philadelphia, Pa.) and from the Central Florida Lions Eye Bank. All corneas were maintained at 4° C. in preservation medium for 1 week or less prior to study. Endothelial cell counts were >2000 cells/$mm^2$. Criteria for exclusion of corneas from these studies included history of endothelial dystrophy, presence of central gutatta, low endothelial cell density, and ocular inflammation or disease.

Ex Vivo Corneal Model

Twenty-one human corneas were obtained from donors of about 52–75 years of age (Avg.=65.1 years old). Whole corneas were usually cut in quarters to increase sample size. In some cases, whole corneas were used as controls. Corneal pieces were placed endothelial-side up in individual wells of a 24-well tissue culture plate (Falcon, Lincoln Park, N.J.). Pieces were incubated for about 24 hrs in Medium-199 containing 10% fetal bovine serum (FBS), 10 ng/ml epidermal growth factor (EGF) (Upstate Biotechnologies, Lake Placid, N.Y.), 20 ng/ml fibroblast growth factor(FGF) (pituitary-derived, Biomedical Research Technologies, Stoughton, Mass.), and 50 mg/ml gentamicin to stabilize the endothelium prior to study. Ethylenediamine tetraacetic acid (e.g., di-sodium EDTA.2 H2O) was prepared in Hank's Balanced Salt Solution (HBSS) without calcium chloride, magnesium chloride, or magnesium sulfate: Life Technologies, Grand Island, N.Y.), adjusted to pH7.4, and added to the culture medium at a final concentration of 0.02, 0.2, or 2.0 mg/ml. Corneas were treated with EDTA for 10, 30, or 60 min and then returned to culture medium for up to 96 hrs. Negative controls for EDTA treatment included exposing corneal pieces to all manipulations and incubation conditions, including 1 hour in HBSS, but without EDTA. All corneas were maintained at 37° C. in a 5% carbon dioxide, humidified atmosphere until removal for analysis of cell cycle progression.

Immunolocalization of ZO-1 and Ki67

Immunostaining for ZO-1 detected corneal endothelial cell boundaries, while Ki67 staining detected actively cycling cells.

Immunolocalization was carried out using the same antibodies and protocols as described previously for ZO-1 (10) and Ki67 (19). Corneal pieces stained for Ki67 were mounted in medium containing propidium iodide (PI: Vector Laboratories, Inc., Burlingame, Calif.) to visualize all nuclei. In some cases, samples were double-stained for both Ki67 and ZO-1. Slides were viewed using a Leica TCS 4D confocal microscope equipped with a Leitz DMRBE laser and SCANware 4.2 software (Leica Lasertechnik, Heidelberg, Germany). Images were collected from the central region of the corneal pieces away from the cut edges using a 16×, 40×, or 100×-oil immersion lens. Laser power and gain controls were adjusted to achieve an optimal range of output signal intensity for each channel. Confocal images were collected and micrographs were printed using Photoshop software v4.0 (Adobe Systems, Inc., San Jose, Calif.). For some micrographs, the printing contrast was adjusted to provide a clearer image.

Evaluation and Quantification of Ki67-Positive Cells

Fluorescence confocal immunocytochemistry for Ki67 was used to evaluate corneal endothelial cells for their ability to enter and complete the cell cycle (i.e., cell proliferation or mitosis). All nuclei were stained with PI. Positive Ki67 staining patterns indicated the presence of actively cycling cells and also acted as markers for specific phases of the cell cycle. Completion of the cell cycle was determined by observation of mitotic figures stained with Ki67. Three representative confocal micrographs were taken per corneal quarter using a 40×-objective lens. An NIH Image v1.62 software program was used to count total PI-stained nuclei, total Ki67-positive cells, and cells in the G1-phase, S/G2-phase, or M-phase of the cell cycle. Cells were counted in five 100-mm$^2$ areas of each micrograph (=15 areas counted per corneal piece). Counts were averaged and the percentage of actively cycling cells and of cells in each phase of the cell cycle was calculated. Each study was conducted using corneas from 2–3 different donors. Statistical comparisons were made by a paired Student's t-test using a StatView v4.11 software program (Abacus Concepts, Inc., Berkeley, Calif.). Results reported in Table 1 were expressed as percentage of Ki67-positive cells +/−SD. Results reported in FIGS. 3B and C were expressed as percentages of Ki67-positive cells, plus or minus standard error (+/−SEM).

Results

Figure Legends

FIG. 1 shows that EDTA decreases the integrity of cell-cell contacts in a dose- and time-dependent manner. Corneal pieces from a 68 year old donor were incubated in the absence of EDTA (A), or in 0.02 (B), 0.2 (C), or 2.0 mg/ml EDTA (D,E) for 30 (B,C,D) or 60 min (E). Normal cell-cell contacts, visualized as an apparent single line of staining between cells, were observed in the absence of EDTA, but a gradual increase in lateral separation occurred with increasing EDTA concentration or incubation time. Arrows in B, C, and D indicate areas of cell-cell separation. Arrows in E indicate thin cytoplasmic strands retained between cells incubated for 60 min in 2.0 mg/ml EDTA. (Original magnification=110×.)

FIG. 2 depicts the stimulation of corneal endothelial cell proliferation requires both preincubation in mitogen-containing medium and treatment with EDTA. Corneal quarters from a 52-year old donor were incubated under the following conditions: A) Incubation for 108 hours in medium containing 10% serum, EGF, and FGF, but without exposure to EDTA. B) No preincubation, 0.2 mg/ml EDTA for 30 min, post-incubation in medium for 48 hrs. C) No preincubation, 2.0 mg/ml EDTA for 30 min, post-incubation in medium for 48 hrs. D) Preincubation for 60 hrs in medium, 0.2 mg/ml EDTA for 30 min, post-incubation for 48 hrs. Positive Ki67 staining was visible only in endothelial cells that were both preincubated and exposed to EDTA. (Note Ki67-positive mitotic figures (arrows) in (D). Original magnification=100×.)

FIG. 3 shows the effects of EDTA on cell cycle kinetics (A) and determination of optimal pre-incubation (B) and post-incubation times (C). To observed cell cycle kinetics in response to EDTA, corneal pieces from a 64 year old donor were pre-incubated for 24 hrs in medium containing 10% serum, EGF, and FGF, then treated with 0.2 mg/ml EDTA for 60 min, followed by post-incubation in the same medium for various periods of time. Results in (A) are expressed as the percent of Ki67-positive cells exhibiting staining patterns for G1 phase, S/G2 phase, or mitosis. To determine optimal pre-incubation time, corneal quarters from a 54 year old donor were pre-incubated in the same medium for different periods of time, followed by 30 minutes of treatment with 2.0 mg/ml EDTA and then an approximately 48-hours post-incubation period. To determine optimal post-incubation time, corneal quarters from a 73 year old donor were pre-incubated in the same medium for 24 hours, followed by approximately 30 minutes of treatment with 2.0 mg/ml EDTA. Quarters were then post-incubated in the same culture medium for different periods of time. Results in (B and C) are expressed as mean+/−SEM.

EDTA's Effects on Corneal Endothelial Cell-Cell Contacts

Studies were first conducted to determine the effect of EDTA on the integrity of endothelial cell-cell contacts. Corneal pieces were incubated for either 10, 30 or 60 minutes, in either 0.02, 0.2, or 2.0 mg/ml EDTA, then washed, and stained for ZO-1 to visualize cell boundaries.

Representative micrographs in FIG. 1 show the dose- and time-dependent effect of EDTA on cell-cell contacts. In the absence of EDTA, cells maintained normal lateral associations (FIG. 1A). With increasing EDTA concentration or incubation time, there was an increase in the lateral separation of cells, visualized as a double line of positive ZO-1 staining demarcating the two cell membranes (FIG. 1B–E). Incubation in the presence of 2.0 mg/ml for 60 minutes caused cells to become rounded with only thin cytoplasmic strands connecting adjacent cells. This treatment, however, did not cause endothelial cells to lose contact with the Descemet's membrane on which the cells were cultured. In contrast, EDTA concentrations over 3.0 mg/ml are not recommended, as they can cause cells to fall off the culture membrane. A most preferred concentration is around 0.2–2.0 mg/ml EDTA. EDTA, at the concentrations and incubation times tested, did not significantly induce cell death as indicated by a commercially available live/dead staining assay (data not shown).

In the method of the invention, exposing corneal endothelial cells to EDTA results in interrupted cell-contacts in at least 15% of treated cells. Typically, this interruption step can produce cell-cell breakages in at least 50%, even at least 80% or more, of corneal endothelial cells thus treated. (Near-complete breakages of cell-cell adhesions, i.e., in nearly all treated cells, have been observed.) It is expected that other calcium chelators can achieve similar results.

EDTA Effects on Cell Cycle Progression

Previous studies (19) revealed that corneal endothelial cells incubated in medium containing 10% serum, 20 ng/ml FGF, and 10 ng/ml EGF stained positively for Ki67 in response to wounding, but no positive staining was observed in unwounded areas of the endothelium. Similarly, Ki67 staining was found lacking, as shown in FIG. 2A, when corneal quarters were incubated in this medium for a total of 108 hours. Thus, exposure of the intact endothelium to this mitogen-containing medium alone was not sufficient to induce cell cycle entry. Similarly, incubation in up to 2.0 mg/ml EDTA alone (i.e., without prior or simultaneous exposure to a growth factor or mitogen) did not promote proliferation, even if cells were subsequently 'post-incubated' for 48 hours in a mitogen-containing medium (FIGS. 2B,C).

In contrast, pre-incubation in mitogen-containing medium and subsequent exposure to EDTA followed by a 48 hour post-incubation did promote cell cycle progression in the corneal endothelium, as revealed by the presence of Ki67 stained nuclei and mitotic figures (FIG. 2D). Negative control corneas were manipulated in a manner similar to EDTA-treated corneas. These corneas were incubated for 1 hour in HBSS alone to control for the EDTA incubation and then maintained for 48 hours in the same culture medium indicated as for the EDAT-treated corneas. Fluorescence microscopy showed only a very rare Ki67-positive cell in corneas cultured in HBSS alone (data not shown).

Ki67 is expressed in cells from mid-to-late G1-phase through mitosis, making it an excellent marker of actively cycling cells (20,21). Immunostaining with antibody to Ki67 also permits semi-quantitative analysis of the relative number of cells in late G1-phase through mitosis (19,22). The graph in FIG. 3A shows typical endothelial cell-cycle kinetics in corneal pieces from a single donor pre-incubated for 24 hours in mitogen-containing medium, treated with 0.2 mg/ml EDTA for 60 min, and post-incubated in medium for 0, 24, 48, or 72 hrs. Cells initiated proliferation by 24 hrs after EDTA treatment and completed the cycle in approximately 48 hrs, as indicated by the presence of mitotic figures at that time point. By 72 hrs after EDTA treatment, there was a mixed population of Ki67-stained cells with evidence of new cell cycle entry. With this method of analysis, it was not possible to determine whether this population of Ki67-positive cells represented a second round of proliferation or whether a sub-population of cells responded more slowly to the EDTA/mitogen treatment. Double-staining of corneal pieces with Ki67 and ZO-1 revealed that cells treated with EDTA and mitogens are capable of completing the cell cycle and forming daughter cells (data not shown).

Determination of Optimal Incubation Conditions

Studies were conducted to determine incubation conditions that induce cell cycle entry in the largest number of endothelial cells as determined by counting Ki67-positive cells.

Figure 3B:
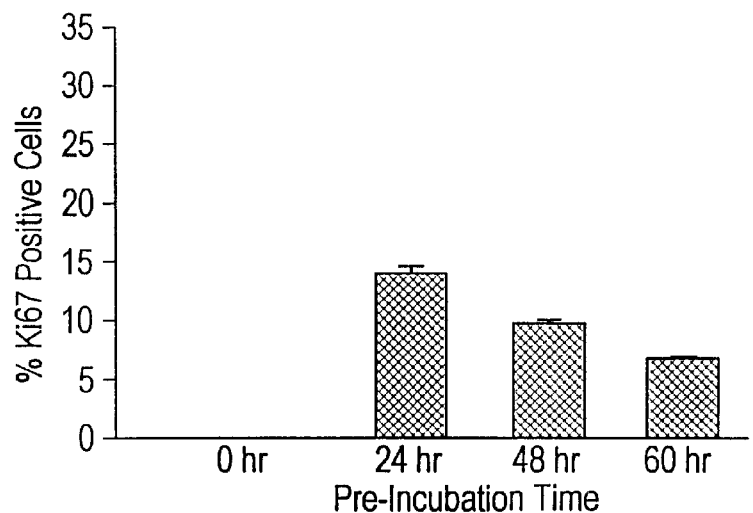

The requirement for pre-incubation of corneas in mitogen-containing medium was first determined. For these studies, pre-incubation times of 0, 24, 48, and 60 hrs were used. EDTA concentration and treatment times were held constant and corneal samples were post-incubated in mitogen-containing medium for 48 hours. FIG. 3B provides a representative example of the results, which indicate that, of the pre-incubation times tested, 24 hrs was sufficient to yield the maximal percentage of Ki67-positive cells. This 24-hour pre-incubation time was then used for all subsequent studies.

Figure 3C:
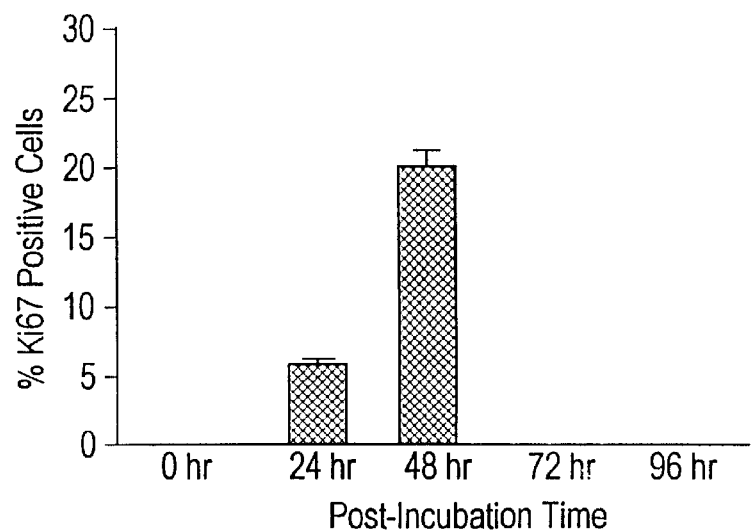

In studies to determine the optimal post-incubation time, corneal pieces were pre-incubated in medium for 24 hrs, followed by EDTA treatment. Post-incubation times tested included 0,24, 48, 72, and 96 hrs. FIG. 3C provides a representative example, indicating that a maximum number of Ki67-positive cells was obtained 48 hrs post-incubation. Depending on the specific donor cornea, some Ki67-positive cells could be detected 72 hrs after EDTA treatment; however, no samples showed actively cycling cells by 96 hr post-incubation.

As indicated in Table 1, EDTA at either 0.2 or 2.0 mg/ml was capable of promoting cell cycle progression. The relative percent of Ki67-positive cells observed under the four EDTA incubation conditions was significantly higher than negative controls in which corneas were incubated in HBSS alone. Corneas treated with 2.0 mg/ml EDTA for 60 min. yielded a significantly higher number of actively cycling cells (p-value=0.007) than those treated with 0.2 mg/ml EDTA for 30 min. Repeated EDTA treatment cycles promoted proliferation over a longer time period, but the treatment became gradually less effective (data not shown).

TABLE I

Effect of EDTA Concentration and Incubation Time on Percent Ki67-Positive Cells

| # | EDTA Concentration | Incubation Time | Avg. % KI67 (+) Cells* SD | P-Value** |
|---|---|---|---|---|
| 1. | 0.2 mg/ml | 30 minutes | 8.67% 2.65 | — |
| 2. | 0.2 mg/ml | 60 minutes | 11.99% 2.63 | 0.13 |
| 3. | 2.0 mg/ml | 30 minutes | 14.28% 6.79 | 0.22 |
| 4. | 2.0 mg/ml | 60 minutes | 17.18% 1.21 | 0.007 | n = 2–3 donor corneas per treatment condition
*= Five 100 $\mu m^2$ were counted/micrograph × 3 micrographs per corneal piece
**= p-value comparison between Avg. % Ki67 (+) cells from condition #1 and other three Ki67 values Discussion The results reported here demonstrates for the first time, that an effective amount of a calcium chelator, specifically EDTA, is able to disrupt lateral cell contacts within the corneal endothelial monolayer without apparent interference with cell-substrate associations or negative effects on viability. Similar results as those obtained with EDTA, are expected with use of other calcium chelators, such as ethylene glycol-bis[β-aminoethylether]-N,N,N',N'-tetraacetic acid (EGTA), used in similar concentrations and under similar conditions.

ZO-1-staining of endothelium treated for 60 minutes with 2.0 mg/ml EDTA (the highest EDTA concentration and longest treatment time tested according to the method of the invention) revealed thin cytoplasmic strands between rounded cells in a pattern very similar to that observed by Stern, et al. (18), who perfused the endothelium with calcium-free medium. Exposure of the intact endothelium to EDTA or to mitogens alone was not sufficient to induce proliferation. In contrast, a combination of the two treatments, with appropriate timing, clearly stimulated a proliferative response. Treatment of the monolayer with EDTA presumably interfered sufficiently with maintenance of junctional complexes to release cells from contact inhibition, making them sensitive to mitogenic stimulation. It is unclear why pre-incubation of the endothelium in mitogen-containing medium was required. Possibly, pre-treatment with mitogens initiates cellular responses that prepare for cell cycle entry once cell-cell contacts have been released. Pre-incubation times shorter than the 24 hrs used in this study may be even more effective, since receptor down-regulation can occur with prolonged growth factor incubation. Optimal pre-incubation times are expected to be in a range of about ??12–18 hours?. The possibility that pre-incubation with mitogens prepares cells to enter the cycle is supported by the fact that cells appeared to initiate proliferation as an almost synchronous population. This response differed from cell cycle entry in wounded endothelium exposed to the same culture medium (19). Under those conditions, cells continued to enter the cycle at different start times until the wound bed was completely repopulated.

An important finding from these studies was that, upon treatment of the intact endothelial monolayer with EDTA and mitogens, around 17% of the cell population entered the cell cycle. The relative percent of Ki67-positive cells tended to differ with the specific treatment used in the experiments. This observation indicates that improved efficiency of the method (i.e., in increasing the percentage of proliferating cells) can be achieved by further refinements to the EDTA and/or mitogen treatment protocol herein described. Such refinements are within the purview of an ordinarily skilled artisan reading this disclosure. The ability to induce proliferation in endothelial cells does not appear to be restricted by the presence of a senescent population, since there was no positive staining for β-galactosidase, a marker of cell senescence(23), in the endothelium samples of older individuals (data not shown).

The induction of proliferation in these experiments occurred without mechanical wounding and without apparent cell damage to the corneas. This underscores the integral role of cell-cell contact in maintaining the corneal endothelium in a non-replicative state. Therefore, temporary interference with this important anti-proliferative mechanism (contact inhibition), could induce transient proliferation in the physiologically important, corneal endothelial monolayer. These findings suggest the possibility of inducing proliferation in adult cornea, thereby increase the density of endothelial cells, by interrupting or interfering with corneal endothelial cell-cell contacts and, preferably previously or simultaneously, exposing the cells to a growth factor promoting corneal endothelial cell growth (e.g., a combination EDTA/mitogen treatment). This treatment could be applied directly to the endothelium in order to increase endothelial cell density in corneas to be used for transplantation. In addition, it may be possible to stimulate endothelial cell division in situ by using a calcium chelator (e.g., EDTA or EGTA), or other reagents that temporarily interfere with cell-cell contact, plus a growth factor or mitogen to increase cell density in individuals at risk for vision loss due to low endothelial cell counts. Other agents useful for disrupting cell-cell adhesions are antibodies directed at an antibody that specifically binds to a cell surface protein on the corneal endothelial cell that is involved in cell-cell adhesion. For instance, the agent could be an antibody that specifically binds to either a cadherin, ZO-1 protein, or connexin-43, the art.

Other Uses of New Medium Formulation for Growing corneal Endothelium

A formulation of the invention, including a calcium chelator as well as serum-free culture medium comprising insulin, transferrin, and selenium; FGF (especially pituitary); EGF; NGF; an anti-biotic antimycotic solution, may be used for the following:

Tissue Culture Medium for Research Purposes-With the use of this medium, researchers can now grow adult human corneal endothelial cells in culture without the need to seed cells onto artificial or cell-derived matrices. Previously, the greatest success in culturing corneal endothelial cells was obtained using corneas from neonates. Clearly, this does not provide a ready supply of tissue for research purposes. The ability to culture cells from older donors (the supply of which is more readily available) will make it possible to conduct molecular and cell biological studies that have been impossible to perform up to now. In addition, use of this medium prevents the need to develop human corneal endothelial cell lines transfected with viral oncogenes or to culture cells from laboratory animals, such as rabbits and rats, in order to obtain sufficient cell numbers for study.

Corneal Storage Medium-This formulation may be useful in preparing donor corneas for transplantation by increasing the number of endothelial cells prior to the transplantation procedure. This may help overcome the loss of endothelial cell density that frequently accompanies normal transplantation.

Ophthalmic Irrigating Solution-This formulation may be useful as an irrigating solution (most likely minus serum) during anterior chamber surgical procedures to maintain the overall health and stability of the endothelium (which can be compromised during these procedures) and to promote proliferation to replace cells damaged during the procedure.

Treatment to Increase Cell Density in Vivo-This formulation may be able to be applied as topical drops or be injected into the anterior chamber to induce transient proliferation of corneal endothelial cells in older individuals whose visual acuity is impaired due to low endothelial cell counts.

Transplantation of Corneal Endothelial Cells to Increase Cell Density. One unique possibility for use of our medium formulation is to culture endothelial cells to increase cell numbers and then transplant the endothelial cell sheet back onto Descemet's membrane to increase cell density. This might be done by transplanting endothelial cells to donor corneas prior to transplantation or by directly applying the cultured endothelial cell sheet to Descemet's membrane of a recipient in vivo.

Development of "Corneal Equivalents". Several laboratories are attempting to develop corneal equivalents for transplantation or for in vitro testing of various cosmetic or pharmacologic agents. Currently, most labs are experimenting with animal corneal endothelial cells or human cells transformed by viral oncogenes, such as SV40. Our medium formulation may make it possible to grow normal, untransformed cells for these corneal equivalents.

Stimulation of Proliferation in Other Ocular and Non-Ocular Cells which Normally Do Not Regenerate—The tissue embryonic origin of the corneal endothelium is neural crest. During fetal development, neural crest cells migrate and then differentiate to form many types of tissue. Many of the cell types formed from neural crest do not readily proliferate in vivo. This formulation may be useful to induce proliferation in other ocular cells of similar origin, including, but not limited to, lacrimal gland acinar cells, ciliary body epithelium, corneal stromal keratocytes, skeletal muscle of the dorsal iris, and trabecular meshwork epithelium. Other non-ocular cells of similar embryonic origin may also proliferate upon exposure to this medium. Among non-ocular cell types of neural crest origin are sensory neurons, Schwann cells associated with the peripheral nervous system, and smooth muscle cells associated with the branchial arch arteries. If this formulation is capable of stimulating any of these cells to divide, it may prove useful as a treatment in repair of damaged tissue.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

REFERENCES

1. Murphy C, Alvarado J, Juster P, Maglio M. Prenatal and postnatal cellularity of the human corneal endothelium. A quantitative histologic study. Invest Ophthalmol Vis Sci. 1984;25:312–322.
2. Laing R A, Sandstrom M M, Berrospi A R, Leibowitz H M. Changes in the corneal endothelium as a function of age. Exp Eye Res. 1976;22:587–594.
3. Wilson S E, Lloyd S A, He Y G, McCash C S. Extended life of human corneal endothelial cells transfected with the SV40 large T antigen. Invest Ophthalmol Vis Sci. 1993;34:2112–2123.
4. Wilson S E, Weng J. Blair S, He Y G, Lloyd S. Expression of E6/E7 or SV40 large T antigen-coding oncogenes in human corneal endothelial cells indicates regulated high-proliferative capacity. Invest Ophthalmol Vis Sci. 1995;36:32–40.
5. Joyce N C, Meklir B, Joyce S J, Zieske J D. Cell cycle protein expression and proliferative status in human corneal cells. Invest Ophthalmol Vis Sci. 1996;37:645–755.
6. Joyce N C, Navon S E, Roy S, Zieske J D. Expression of cell cycle-associated proteins in human and rabbit corneal endothelium in situ. Invest Ophthalmol Vis Sci. 1996;37:1566–1575.
7. Tripathi, R. C., Borisuth, N. S. C., Tripathi, B. J. and Fang, V. S. Analysis of human aqueous humor for epidermal growth factor. Exp. Eye Res. 1991;53:407–409.
8. Harris D L, Joyce N C. Transforming growth factor-b suppresses proliferation of rabbit corneal endothelial cells in vitro. J Interferon Cytokine Res. 1999;19:327–334.
9. Chen K H, Harris D L, Joyce N C. TGF-b2 in aqueous humor suppresses S-phase entry in cultured corneal endothelial cells. Invest Ophthalmol Vis Sci.1999;40:2513–2519.
10. Joyce N C, Harris D L, Zieske J D. Mitotic inhibition of corneal endothelium in neonatal rats. Invest Ophthalmol Vis Sci.1998;39:2572–2583.
11. Treffers W F. Human corneal endothelial wound repair: In vitro and in vivo. Ophthalmol. 1982; 1989:605–613.
12. Hoppenreijs V P K, Pels E, Vrensen G F, Oosting J, Treffers W F. Effects of human epidermal growth factor on endothelial wound healing of human corneas. Invest Ophthalmol Vis Sci. 1992;33:1946–1957.
13. Hirano S, Nose A, Hatta K, Kawakami A, Takeichi M. Calcium-dependent cell-cell adhesion molecules (cadherins): subclass specificities and possible involvement of actin bundles. J Cell Biol. 1987;105:2501–2510.
14. Siliciano J D, Goodenough D A. Localization of the tight junction protein, ZO-1, is modulated by extracellular calcium and cell-cell contact in Madin-Darby canine kidney epithelial cells. J Cell Biol. 1988;107:2389–2399.
15. Jongen W M, Fitzgerald D J, Asamoto M, Piccoli C, Slaga T F, Gros D, Takeichi M, Yamasaki H. Regulation of connexin 43-mediated gap junctional intercellular communication by Ca2+ in mouse epidermal cells is controlled by E-cadherin. J Cell Biol. 1991;114:545–555.
16. Kaye G I, Mishima S, Cole J D, et al. Studies on the cornea. VII. Effects of perfusion with a Ca++-free medium on the endothelium. Invest Ophthalmol. 1968;7:53–66.
17. Kaye G I, Hoefle F B, Donn A. Studies on the cornea. VIII. Reversibility of the effects of in vitro perfusion of the rabbit corneal endothelium with calcium-free medium. Invest Ophthalmol. 1973;12:98–113.
18. Stern M E, Edelhauser, H F, Pederson H J, Staatz W D. Effects of ionophores X537A and A23187 and calcium-free medium on corneal endothelial morphology. Invest Ophthalmol Vis Sci. 1981;20:497–508.
19. Senoo T, Joyce N C. Stimulation of human cell cycle progression in human corneal endothelium. Invest Ophthalmol Vis Sci. In press.
20. Gerdes J, Li L, Schluter C, et al. Immunobiochemical and molecular biologic characterization of the cell proliferation-associated nuclear antigen that is defined by monoclonal antibody Ki-67. Am J Pathol. 1991;38:867–873.
21. Verheijen R, Kuijpers H J H, Driel R, Beck J L M, Dierendonck J H, Brakenhoff G J, Ramaekers F C S. Ki-67 detects a nuclear matrix-associated proliferation-related antigen: Localization in mitotic cells and association with chromosomes. J Cell Sci. 1989;92:531–540.
22. Kill I R, Faragher R G, Lawrence K, Shall S. The expression of proliferation-dependent antigens during the lifespan of normal and progeroid human fibroblasts in culture. J Cell Sci. 1994;107:571–579.
23. Dimri G P, Lee X, Basile G, et al. A biomarker that identifies senescent human cells in culture and in aging skin in vivo. Proc Natl Acad Sci USA. 1995;92:9363–9367.

What is claimed as the invention is:

1. A method of stimulating proliferation of adult human corneal endothelial cells, comprising:

exposing adult human corneal endothelial cells to an effective amount of at least one growth factor that promotes proliferation of corneal endothelial cells; and subsequently exposing the adult human corneal endothelial cells to an effective amount of at least one agent that promotes interruption of cell-cell contacts between adjacent corneal endothelial cells.

2. The method of claim 1, further comprising, subsequent to the cell-cell contact interrupting step, exposing the adult human corneal endothelial cells again to the at least one growth factor.

3. The method of claim 1, wherein the adult human corneal endothelial cells are in a form selected from the group consisting of a corneal cell culture, a corneal tissue culture, a corneal organ culture, an intact cornea, and an intact eye.

4. The method of claim 1, wherein the at least one agent comprises a calcium chelator.

5. The method of claim 4, wherein the calcium chelator is ethylenediaminetetraacetic acid (EDTA) or ethylene glycol-bis[β-aminoethylether]-N,N,N',N'-tetraacetic acid (EGTA).

6. The method of claim 4 or claim 5, wherein the agent is administered to the corneal endothelial cells in a concentration within a range of about 0.02–3.0 mg/ml.

7. The method of claim 4 or 5, wherein the agent is administered to the adult human corneal endothelial cells in a concentration within a range of about 0.2–2.0 mg/ml.

8. The method of claim 1, wherein the agent is an antibody that specifically binds to a cell surface protein on the corneal adult human corneal endothelial cell that is involved in cell-cell adhesion.

9. The method of claim 8, wherein the agent is an antibody that specifically binds to a protein selected from the group consisting of a cadherin, ZO-1 protein, and connexin-43.

10. The method of claim 1, wherein the interruption step results in an interruption in cell-cell contacts in at least 15% of the adult human corneal endothelial cells.

11. The method of claim 1, wherein the interruption step results in an interruption in cell-cell contacts in at least 50% of the adult human corneal endothelial cells.

12. The method of claim 1, wherein the interruption step results in an interruption in cell-cell contacts in at least 80% of the adult human corneal endothelial cells.

* * * * *

UNITED STATES PATENT AND TRADEMARK OFFICE
CERTIFICATE OF CORRECTION

PATENT NO. : 6,548,059 B1
DATED : April 15, 2003
INVENTOR(S) : Nancy C. Joyce et al.

It is certified that error appears in the above-identified patent and that said Letters Patent is hereby corrected as shown below:

Column 5,
Line 58, "110x." should read -- 100x. --; and

Column 12,
Line 51, "the corneal adult human" should read -- the adult human --.

Signed and Sealed this

Nineteenth Day of October, 2004

JON W. DUDAS
*Director of the United States Patent and Trademark Office*